(12) United States Patent
Braun et al.

(10) Patent No.: US 6,985,766 B2
(45) Date of Patent: Jan. 10, 2006

(54) APPARATUS AND METHOD FOR POSITIONING MEDICAL TREATMENT DEVICES OR TREATMENT SUPPORTING DEVICES

(75) Inventors: Richard Braun, München (DE); Robert Schmidt, München (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 419 days.

(21) Appl. No.: 09/770,830

(22) Filed: Jan. 26, 2001

(65) Prior Publication Data
US 2001/0044577 A1 Nov. 22, 2001

(30) Foreign Application Priority Data
Jan. 26, 2000 (DE) .................................. 100 03 269

(51) Int. Cl.
A61B 5/05 (2006.01)

(52) U.S. Cl. .................. 600/424; 600/407; 600/410; 600/411; 600/417; 600/421; 600/423; 324/306; 324/307; 324/318; 324/322; 250/256; 378/20; 378/42

(58) Field of Classification Search .............. 600/407, 600/410, 411, 417, 421, 423, 424, 473, 476; 378/20, 42; 250/256; 324/306, 307, 318, 324/322, 305
See application file for complete search history.

(56) References Cited

U.S. PATENT DOCUMENTS

| 5,402,801 | A | * | 4/1995 | Taylor ................... 128/898 |
| 5,445,166 | A | * | 8/1995 | Taylor ................... 128/897 |
| 5,695,500 | A | * | 12/1997 | Taylor et al. ............ 606/130 |
| 5,865,744 | A | * | 2/1999 | Lemelson ................ 600/407 |
| 5,950,629 | A | * | 9/1999 | Taylor et al. ............ 128/897 |
| 5,976,156 | A | * | 11/1999 | Taylor et al. ............ 606/130 |
| 6,128,522 | A | * | 10/2000 | Acker et al. ............. 417/312 |
| 6,231,526 | B1 | * | 5/2001 | Taylor et al. ............ 600/587 |
| 6,404,202 | B1 | * | 6/2002 | Damadian et al. ....... 324/300 |
| 6,405,072 | B1 | * | 6/2002 | Cosman .................. 600/426 |
| 6,414,490 | B1 | * | 7/2002 | Damadian et al. ....... 324/319 |
| 6,534,982 | B1 | * | 3/2003 | Jakab ..................... 324/318 |
| 2002/0065461 | A1 | * | 5/2002 | Cosman .................. 600/426 |

FOREIGN PATENT DOCUMENTS

DE  19823260 A1  12/1999
DE  29907990 U1   1/2000

OTHER PUBLICATIONS

Krankenhaus Technik: Unermüdlicher Mitarbeiter, Sep. 1997, p. 50.

JP 07204255 A (Abstract), JAPIO (recherchiert am Dec. 15, 2000). In: STN.

* cited by examiner

Primary Examiner—Brian L. Casler
(74) Attorney, Agent, or Firm—Renner, Otto, Boisselle & Sklar, LLP

(57) ABSTRACT

The invention refers to an apparatus for positioning medical treatment devices or treatment supporting devices (2) by a transportation means (1) to move said devices (2) to a predetermined position, said transportation means (1) including an automatically guided transport system (3, 7), and to a corresponding method and the use of an automatically guided transport system to perform said positioning tasks.

17 Claims, 2 Drawing Sheets

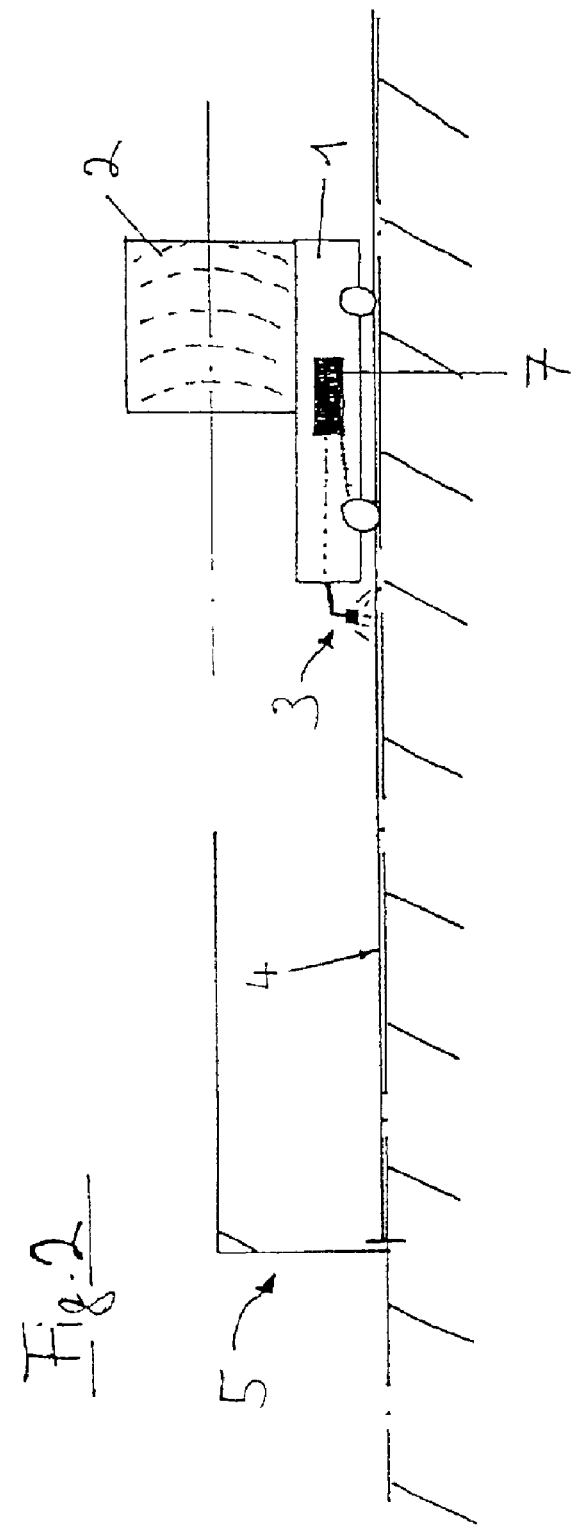

APPARATUS AND METHOD FOR POSITIONING MEDICAL TREATMENT DEVICES OR TREATMENT SUPPORTING DEVICES

BACKGROUND OF THE INVENTION

1. Technical Field

The present invention refers to an apparatus and a method for positioning medical treatment devices or treatment supporting devices, which are moved to a predetermined position by a transportation means.

In operating rooms and surgeries or rooms where operations or treatments are prepared, it is often required to move treatment devices or treatment supporting devices to precisely predetermined positions, either to verify a treatment result by means of computer tomography or nuclear spin tomography or, quite simply, to set-up a specific operating set for the respective surgeon concerned. In the latter case, at present all conceivable devices are moved in the operating theater by auxiliary staff to the position desired by the surgeon, which involves considerable effort.

If image-generating devices are to be used for intra-operative purposes to verify the treatment result or to update an operating navigation, it is even more complicated to move the required devices to the position there where they are needed. It is, for example, very difficult to manually move a mobile nuclear spin tomographic device so as to be precisely parallel over an operating table, as such a device is very heavy and its free internal diameter is usually just a little bit larger than the operating table's width, so that the device can only be moved manually on rolls very slowly and requires a high expenditure of energy; the danger still being that the tomograph may be tilted at the operating table.

2. Description of Related Art

To avoid this problem, it has become common use to move nuclear magnetic resonance (NMR) tomographs over the operating table and away therefrom on a rail mounted to the room ceiling, the operating table being firmly fixed in the room opposite to said rail. This solution involves both constructional and architectonic efforts (strengthening of the ceiling, static expertise . . . ) so that a room cannot be used for some time.

SUMMARY OF THE INVENTION

It is an object of the present invention to provide an apparatus and a method for positioning medical treatment devices or treatment supporting devices which overcomes the above-mentioned disadvantages. In particular, a flexible adaptive positioning system should be provided which enables uncomplicated positioning of the devices.

According to the invention, this object is first of all solved by an apparatus for positioning medical treatment devices or treatment supporting devices by a transportation means used to move said devices to a predetermined position, the transportation means comprising an automatically guided transport system. Such an automatically guided transport system controls the movement of a device from one position to another in a self-guiding and self-driven manner. Accordingly, the devices can be moved in the room automatically without any manual movement being required. Such automatically guided transport systems (also called "automatic guided vehicles") navigate in the room without assistance and, in contrast to the above-mentioned rail systems, can advantageously be moved on the ground without any larger obstacles, where a person might stumble, in the form of rails being constructed on the ground. Furthermore, it is in principle possible to set a surgeon-specific operating set by pressing a button, as generally all conceivable treatment devices and treatment assisting devices can be moved to predetermined positions by means of an automatically guided transport system.

In an embodiment in accordance with the invention, the transportation means includes a movable vehicle, on which the device to be moved is positioned. Using such a vehicle, even heavy devices, for example heavy nuclear spin tomographic devices, can also be positioned easily.

The automatically guided transport system may include, if used according to the invention, one of the following navigation systems:

1. Optical tracking, particularly by means of a ground guidance band, actual value markers as well as an optical sensor and a path measuring system provided at the transportation means. In such a navigation system, a guidance band, stuck to the ground, is recognized by an optical sensor provided in or at the vehicle. In particular, the different in contrast at an edge of the band is detected here. This solution is simple, inexpensive and does not damage the ground. There are no restrictions due to cable ducts or steel plates. The operator can change the driving route very flexibly, with no program changes being required. Accordingly, optical tracking is especially suitable where routes have to be changed very often, thus increasing the flexibility of the positioning system in accordance with the invention. Depending on the task and the surroundings, different guidance bands can be provided, and optical tracking does not depend on inclines, slopes and undulations of the ground floor. The indifference of optical tracking, in particular to strong magnetic fields as they arise, for example, during the use of MR imaging devices, is also very advantageous. Moreover, such tracking is indifferent to light and shocks.

2. Laser navigation, particularly by means of a laser, reflectors and a path measuring system provided at the transportation means.
   This laser navigation system without guiding wire scans the surroundings by means of a laser beam; the driving route being programmed. Advantageously, no ground installations are required meaning that this system can also be used for very dust-sensitive applications. Besides, this system is also very flexible with regard to driving route changes, as it is just required to change the program. Owing to permanent route correction, a high driving accuracy is given, and the system is indifferent to light, heat and shocks as well as to magnetic fields.

3. Magnetic navigation, particularly by means of a ground floor magnetic track, as well as a magnetic strip, gyroscope and path measuring system provided at the transportation means.
   If devices without inherent magnetic fields are to be moved, this is a suitable system, which also works with a programmed driving route and is, therefore, very flexible with regard to driving route changes; if necessary, additional magnets should be used. Only minimal ground installations in the form of small reference magnets are required and there are no restrictions due to ground obstacles. The system is indifferent to inclines, slopes and undulations of the ground floor as well as to light, heat, shocks and dust.

4. Inductive guidance, particularly by means of a ground guiding wire with frequency generator, actual value generators as well as driving and steering antennae and a path measuring system provided at the transportation means.
   In this case, a very high degree of driving accuracy is attained due to permanent route correction, and the system, on the whole, is inexpensive. In addition to being independent of inclines, slopes and undulations of the ground floor, this guidance is also indifferent to light, heat and shocks.

In a preferred embodiment, the device to be positioned is a mobile nuclear spin tomographic device which, as already mentioned above, up until now could only be moved with rail guides, provided at the ceiling. In accordance with the invention, such a mobile nuclear spin tomography device can now be moved on the ground and, thus, is available without much effort being involved. In this connection, smaller tomographic devices are already available on the market, which have a weight of approximately one ton and are equipped with super-conductive coils in order to be able to entirely switch the magnetic field on or off at a relatively fast speed. Devices operating with a magnetic flux density of about 0.5 T may be used. The range of flux density is solely restricted by the size and weight of the nuclear tomographic device, a result of the current magnetic technology. The greater the magnetic flux density, the faster and better the scanning process. Accordingly, if magnets of greater flux density and of a still mobile weight are available, they might readily be used within the scope of the invention.

It is, of course, possible to position all conceivable devices, especially those provided in an operating theater, by means of an apparatus according to the invention. The following is an incomplete list of such devices: a device used for computer tomography, an x-ray bow, a microscope, in particular a surgical microscope, an operating table, a surgeon's stool, a treatment navigation system. Accordingly, if all conceivable devices are positioned in the treatment or operating room, a surgeon-specific operating set can basically be provided by pressing a button. To do so, the transport system is preferably directly arranged at the transportation means and includes a radio or wire interface to an external control. Thus, the surgeon concerned, for example, may enter a simple command to instruct a central treatment supporting device, e.g. a touch screen navigation device, to position a treatment device automatically. This may be, for example, the request to perform an intra-operative nuclear spin tomographic scan.

According to the method for positioning medical treatment devices or treatment supporting devices in accordance with the invention, the devices are moved to a predetermined position by a transportation means, which is steered by an automatically guided transport system. The above statements concerning the advantages of the inventive apparatus can also be transferred to the method. The same applies to the use of an automatically guided transport system for positioning treatment devices or treatment supporting devices in accordance with the invention.

The invention will now be explained in detail by means of a preferred embodiment.

BRIEF DESCRIPTION OF THE DRAWINGS

FIG. 1 is a top view of an automatically guided moved nuclear spin tomographic device and its movement over an operating table, whereas FIG. 2 is a side view of this arrangement.

DETAILED DESCRIPTION OF THE PREFERRED EMBODIMENTS

Figure 1:
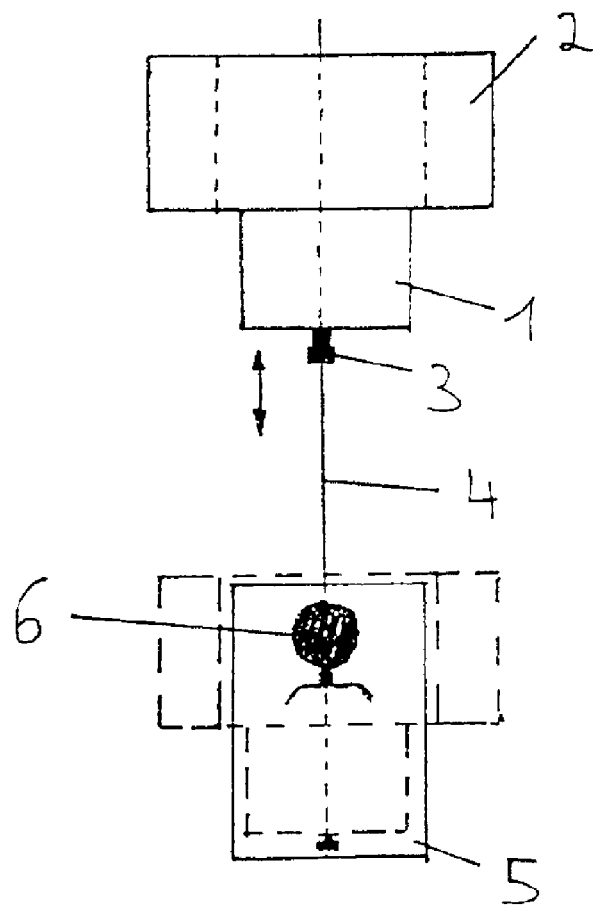

As can be seen from FIGS. 1 and 2, the positioning system according to the invention functions with the following elements:

An automatically guided transport system (FTS) is accommodated in a vehicle 1 with a central unit 7, here being shown as black box, as well as an optical sensor 3, mounted to the front of the vehicle. The central unit 7 receives positioning signals from sensor 3 and steers the vehicle 1 using such data. This is shown by dotted lines leading from the central unit 7 to optical sensor 3 and to a front wheel, the latter line indicating that steering and driving of the vehicle is controlled by the central unit 7.

A mobile nuclear spin tomographic device 2 is positioned on the vehicle. Said device 2 is positioned with regard to its height so that the center axis of the coils thereof is of approximately the same height as the operating table 5. The internal free diameter of coils 2 is slightly larger than the width of the table, as can especially be seen from FIG. 1. According to the top of FIG. 1, the vehicle 1 with the device 2 is first of all shown in a waiting position, while the dotted lines also show the vehicle in its scanning position at operating table 5. The bottom view particularly shows that the tomographic device is here positioned above the patient's head to generate a corresponding image. The head is shown schematically and is allocated the reference number 6.

The automatically guided transport system is guided via the ground guidance band 4, which may, e.g., be a black band on a light ground. The difference in contrast is sensed by the optical sensor 3 at one border of the band and the positioning data is passed on to the central unit 7, which, in turn, steers the vehicle 1 so that it can move precisely in the middle over the guidance band 4 in the direction of the arrow (see FIG. 1). Such steering of the automatically guided transport system can be triggered by radio or by a cable connection (not shown). In FIG. 2, the left end of the guidance band 4 is underneath the table, i.e., in the present case, the vehicle 1 will stop moving if the sensor 3 detects this end of the guidance band.

The following explains once again how the inventive positioning of devices in an operating theater can be performed by way of an example of the sequence of events:

If, for example, a surgeon determines during a cerebral operation that it is time to perform an intermediate check-up of the operational result by means of an NMR imaging device, or to update his navigation system due to positional changes of parts of the tissue, he can press a button, provided at his navigation console, so as to request movement of the NMR device to the spot, either via a radio signal or a cable connecting the vehicle 1 to the console (not shown).

Now, the vehicle 1, including the device 2, is moved at a speed of approximately 0.3 m/s to a pre-position, which is relatively near the operating table, such that the device 2 with its coils is already arranged completely parallel to the table and in axial direction thereto. Parallelism is continuously checked by means of laser triangulation. The magnetic field is not active during transportation.

At this point, it should be noted that markers are fixed preferably to the ground in the operating theater, respectively indicating 50 spaced gauss lines and 5 gauss lines. Such markers help to reliably place magneto-sensitive equipment, and equipment made of metal, at a safe distance.

As soon as the pre-position has been reached, precision positioning will be carried out, the device 2 on the vehicle 1 being moved stepwise over the patient's head 6 to the final position. Likewise, parallelism is continuously checked by means of laser triangulation while accurate positioning is being done. Now, MR scanning (nuclear spin tomography) can be performed.

At the end of such scanning, the above steps can be performed in reverse order to return the device to its standby position (see top of FIG. 1) so that the surgeon can proceed his work with the assistance of the newly acquired data.

Generally, it is to be noted that all positioning tasks in the system in accordance with the invention can also (additionally) be solved by including navigation systems usually available in modern operating rooms, such as, for example, a reflector referencing system including infrared cameras.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. An apparatus for positioning at least one medical treatment device or treatment supporting device comprising a transporting means to move said device to a predetermined position, wherein said transportation means includes a movable vehicle on which said device is positioned and an automatically guided transport system, and wherein said automatically guided transport system comprises at least one of the following navigation systems;
   an optical tracking navigation system;
   a laser navigation system;
   a magnetic navigation system;
   an inductive guidance navigation system; and
wherein said transport system is a laser navigation system, and said laser navigation system includes a laser, reflectors and a path measuring system.

2. The apparatus as set forth in claim 1, wherein said device is a nuclear spin tomograph.

3. The apparatus as set forth in claim 2, wherein said nuclear spin tomographic device comprises superconductive coils of a magnetic flux density of approximately 0.5 Tesla.

4. The apparatus as set forth in claim 1, wherein said device is one of the following:
   a device related to computer tomography;
   an x-ray bow;
   a microscope;
   an operating table;
   a surgeon's stool;
   a treatment navigation device;
   an anesthesia-related device;
   a vehicle for accessories;
   an autoclave device;
   a patient-supervising monitor;
   a sterile material.

5. The apparatus as set forth in claim 1, wherein said transport system includes a control unit carried by said vehicle, and said control unit includes a radio or wire interface for external control.

6. The apparatus as set forth in claim 1, wherein said movable vehicle is self-driven.

7. The apparatus as set forth in claim 1, wherein the device is an image-generating device.

8. A method for positioning a mobile nuclear spin tomographic device, comprising the steps of moving said device to a predetermined position by a transportation means including a movable vehicle on which the device is carried, wherein said transportation means is controlled by an automatically guided transport system; and wherein said automatically guided transport system uses at least one of the following navigation systems for steering purposes:
   an optical tracking navigation system;
   a laser navigation system;
   a magnetic navigation system;
   an inductive guidance navigation system.

9. The method as set forth in claim 8, wherein one of the following devices is being transported:
   a device related to computer tomography;
   an x-ray bow;
   a microscope, particularly a surgical microscope;
   an operating table;
   a surgeon's stool;
   a treatment navigation device;
   an anesthesia-related device;
   a vehicle for accessories;
   an autoclave device;
   a patient-supervising monitor;
   a sterile material.

10. The method as set forth in 8, wherein said transport system is provided on said vehicle and is externally activated via a radio or wire interface.

11. The method as set forth in claim 8, wherein the vehicle is self-driven.

12. An apparatus for positioning at least one medical treatment device or treatment supporting device comprising a transportation means to move said device to a predetermined position, wherein said transportation means includes an automatically guided transport system, and wherein said automatically guided transport system comprises an optical tracking navigation system, and said optical tracking navigation system includes a ground guidance band and an optical sensor for sensing the ground guidance band.

13. The apparatus as set forth in claim 12, wherein the optical tracking navigation system includes a path measuring system.

14. An apparatus for positioning at least one medical treatment device or treatment supporting device comprising a transportation means to move said device to a predetermined position, wherein said transportation means includes an automatically guided transport system, and wherein said automatically guided transport system comprises a magnetic navigation system, and said magnetic navigation system includes a ground floor magnetic track or magnetic strip and a path measuring system.

15. An apparatus for positioning at least one medical treatment device or treatment supporting device comprising a transportation means to move said device to a predetermined position, wherein said transportation means includes an automatically guided transport system, and wherein said automatically guided transport system comprises an inductive guidance navigation system, and said inductive guidance navigation system includes a ground guidance wire with a frequency generator, and a steering antenna.

16. The apparatus as set forth in claim 15, wherein the inductive guidance navigation system includes a path measuring system.

17. A method for positioning at least one medical treatment device or treatment supporting device, comprising the steps of moving said device to a predetermined position by a transportation means, wherein said transportation means is controlled by an automatically guided transport system; and wherein said automatically guided transport system uses at least one of the following navigation systems for steering purposes:
   an optical tracking navigation system;
   a laser navigation system;

a magnetic navigation system;
an inductive guidance navigation system; and
wherein said device is moved to a pre-position at a first speed and then moved from the pre-position to an operative position at a slower speed for more precise positioning of the device at the operative position.

* * * * *